United States Patent
Harada et al.

(10) Patent No.: US 8,634,634 B2
(45) Date of Patent: Jan. 21, 2014

(54) DEFECT OBSERVATION METHOD AND DEFECT OBSERVATION APPARATUS

(75) Inventors: Minoru Harada, Fujisawa (JP); Ryo Nakagaki, Kawasaki (JP); Kenji Obara, Kawasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 201 days.

(21) Appl. No.: 13/146,032

(22) PCT Filed: Dec. 21, 2009

(86) PCT No.: PCT/JP2009/071208
§ 371 (c)(1),
(2), (4) Date: Aug. 8, 2011

(87) PCT Pub. No.: WO2010/098004
PCT Pub. Date: Sep. 2, 2010

(65) Prior Publication Data
US 2011/0299760 A1    Dec. 8, 2011

(30) Foreign Application Priority Data
Feb. 25, 2009 (JP) ................. 2009-042499

(51) Int. Cl.
G06K 9/00    (2006.01)
(52) U.S. Cl.
USPC ........................................ 382/145
(58) Field of Classification Search
USPC ............... 382/141–145, 149; 348/92, 125
See application file for complete search history.

(56) References Cited

U.S. PATENT DOCUMENTS

| | | | | |
|---|---|---|---|---|
| 5,995,219 A * | 11/1999 | Tabata | ....................... | 356/237.5 |
| 6,476,388 B1 * | 11/2002 | Nakagaki et al. | ................. | 850/9 |
| 7,173,693 B2 * | 2/2007 | Shibata et al. | ............. | 356/237.1 |
| 7,257,247 B2 * | 8/2007 | Bruce et al. | ................... | 382/144 |
| 7,664,307 B2 * | 2/2010 | Saito | ............................. | 382/144 |
| 8,175,373 B2 * | 5/2012 | Abbott et al. | ................. | 382/149 |
| 2006/0038986 A1 | 2/2006 | Honda et al. | | |
| 2007/0031026 A1 | 2/2007 | Kurihara et al. | | |

FOREIGN PATENT DOCUMENTS

| | | |
|---|---|---|
| JP | 2000-067243 | 3/2000 |
| JP | 2003-098114 | 4/2003 |
| JP | 2004-109788 | 4/2004 |
| JP | 2005-061837 | 3/2005 |
| JP | 2007-40910 | 2/2007 |
| JP | 3893825 | 3/2007 |

* cited by examiner

*Primary Examiner* — Daniel Mariam
(74) *Attorney, Agent, or Firm* — Antonelli, Terry, Stout & Kraus, LLP.

(57) ABSTRACT

Provided is a defect observation apparatus capable of analyzing a structure such as an arrangement and a vertical relationship of a circuit pattern formed by using design information of a sample, creating a non-defective product image from a defect image based on the analysis results, and detecting a defect by comparative inspection. The defect observation apparatus is provided with a computing unit 120 which receives an input regarding design information of a sample 106 to be observed from a storage unit 114, receives an input regarding observable layer information previously set to the sample to be observed from the storage unit 114 based on the design information including one or more layers, receives an input regarding defect coordinates on the sample detected by another inspection apparatus from the storage unit 114, analyzes, for a defect on the sample 106 to be observed based on the defect coordinates, a circuit pattern structure in a peripheral area of the defect coordinates based on the design information and the layer information, estimates a non-defective product image based on the analysis result of the circuit pattern structure, and detects a defect by a comparative inspection between the non-defective product image and image information from an image obtaining unit.

10 Claims, 9 Drawing Sheets

DEFECT OBSERVATION METHOD AND DEFECT OBSERVATION APPARATUS

TECHNICAL FIELD

The present invention relates a defect observation method and a defect observation apparatus for observing a defect and others on a sample, and more particularly to an improvement in throughput thereof.

BACKGROUND ART

For the improvement in yields of semiconductors, it has become important to immediately clarify the cause of occurrence of a defect in manufacturing process. At present, at the site of manufacturing semiconductors, defect analysis is performed by using a defect inspection apparatus and a defect observation apparatus.

The defect inspection apparatus is an apparatus that observes a wafer with optical means or electron beams and outputs detected defect coordinates. Since it is important for the defect inspection apparatus to process a wide range at high speed, the amount of image data is reduced by increasing the pixel size of an image to be obtained as much as possible (that is, by decreasing resolution). Therefore, in many cases, while the presence of a defect can be confirmed from the detected low-resolution image, the type of the defect cannot be determined in detail.

Thus, the defect observation apparatus is used. The defect observation apparatus is an apparatus that takes an image of defect coordinates of the wafer at high resolution based on the output from the defect inspection apparatus and outputs the image. With the advance of microfabrication in the semiconductor manufacturing process, the defect size has reached the order of several tens of nm, and a resolution power on the order of several nm has been required in order to observe the defect in detail.

For this reason, a defect observation apparatus using a scanning electron microscope (review SEM) has been widely used in recent years.

In a mass-production line of semiconductors, automation of observation operation is desired, and the review SEM has an ADR (Automatic Defect Review) function of automatically collecting the images at defect coordinates in a sample.

ADR is a function of automatically collecting the images of defect parts taken at a high magnification based on defect coordinates obtained from the defect inspection apparatus. The problem to be solved here is an error between defect coordinates output from the defect inspection apparatus and actual defect coordinates.

In general, since a variation of about ±4 [μm] is present as an error, when taking an image of the defect coordinates output from the defect inspection apparatus at a high magnification with a field of view of about 2.5 [μm] (for example, 50,000 times), there is a possibility that a defect may not be within the field of view.

For its solution, an image is first taken at a first magnification with a field of view of about 9 [μm] (for example, 15,000 times), a defect is next detected from the low-magnification image, and finally, an image of the detected defect is taken at a second magnification (for example 50,000 times).

Japanese Patent No. 3893825 (Patent Document 1) discloses, as a defect detecting method, a comparative inspection method in which a defect image obtained by taking an image of a defect part at a low magnification and a non-defective product image obtained by taking an image of a part where the same pattern as that of the defect part is formed at a low magnification are compared and a difference between these two images is detected as a defect.

Since a plurality of same chips are arranged on a semiconductor wafer, an image obtained by taking an image of a location moved by one chip from the coordinates where a defect is present can be used as a non-defective product image.

In recent years, with an increase in diameter of a semiconductor wafer, the number of defects to be reviewed per one wafer is increased, and the throughput of the review SEM is lower than that of the defect inspection apparatus. For these reasons, speed-up of ADR has been required.

In general, it takes a large amount of time for ADR to move a stage from an initial position to a destination position and take a non-defective product image and a defect image. A method of not only speeding up these processes but also omitting some of them in the image-taking procedure is effective for the speed-up of ADR.

Normally, the process in the procedure to be omitted is a process of taking a non-defective product image. For example, a method of previously preparing a non-defective product image and a method of synthesizing a non-defective product image from a defect image and performing a comparative inspection have been suggested.

As an example of the former method, as disclosed in Japanese Unexamined Patent Application Publication No. 2000-67243 (Patent Document 2), there is a method in which a cyclic pattern is previously stored in a memory area or the like as a non-defective product image and a comparative inspection is performed by using this image and a defect image, thereby detecting a defect.

As an example of the latter method, as disclosed in Japanese Unexamined Patent Application Publication No. 2003-98114 (Patent Document 3), there is a method in which local areas or the like with a similar appearance on a defect image are compared, a normal part is detected based on a probability distribution, a degree of reliability of a differential area with respect to defect detection is calculated, and the differential area with a high degree of reliability is detected as a defect. In addition, as disclosed in Japanese Unexamined Patent Application Publication No. 2007-40910 (Patent Document 4), there is a method in which a repeated cycle of a circuit pattern taken in a defect image is used to synthesize a non-defective product image, and a defect is detected by a comparative inspection with the synthesized non-defective product image.

PRIOR ART DOCUMENTS

Patent Documents

Patent Document 1: Japanese Patent No. 3893825
Patent Document 2: Japanese Unexamined Patent Application Publication No. 2000-67243
Patent Document 3: Japanese Unexamined Patent Application Publication No. 2003-98114
Patent Document 4: Japanese Unexamined Patent Application Publication No. 2007-40910

SUMMARY OF THE INVENTION

Problems to be Solved by the Invention

For detecting a defect on a sample with high throughput, it is effective to omit the imaging-taking process of a non-defective product image. Patent Document 3 discloses a method of detecting a defect without a non-defective product image. In the method described in Patent Document 3, the defect image is divided into local areas, areas designed to have the same appearance as each local area are searched based on design information of a circuit pattern formed on the sample, and a non-defective product image is created from the defect image. However, it does not describe the method of taking into account a plurality of layers included in the design information when the local areas are searched based on the design information.

Moreover, although Patent Document 4 is published as a method of automatically determining whether a reference-free method can be applied based on a taken image, since a determination is made based on a taken image in Patent Document 4, it has a problem that the result tends to be influenced by image quality.

Therefore, an object of the present invention is to provide a defect observation method and a defect observation apparatus capable of analyzing a structure such as an arrangement and a vertical relationship of a circuit pattern formed by using design information of a sample, creating a non-defective product image from a defect image based on the analysis results, and detecting a defect by comparative inspection.

The above and other objects and novel characteristics of the present invention will be apparent from the description of the present specification and the accompanying drawings.

Means for Solving the Problems

The following is a brief description of an outline of the typical invention disclosed in the present application.

That is, a general outline of the typical aspect is a defect observation apparatus provided with a computing unit which receives an input regarding design information of a sample to be observed from a storage unit, receives an input regarding observable layer information previously set to the sample to be observed from the storage unit based on the design information including one or more layers, receives an input regarding defect coordinates on the sample detected by another inspection apparatus from the storage unit, analyzes, for a defect on the sample to be observed based on the defect coordinates, a circuit pattern structure in a peripheral area of the defect coordinates based on the design information and the layer information, estimates a non-defective product image based on the analysis result of the circuit pattern structure, and detects a defect by a comparative inspection between the non-defective product image and image information from an image obtaining unit.

Effects of the Invention

The effects achieved by a typical aspect of the invention disclosed in the present application will be briefly described below.

That is, an effect to be achieved by the typical aspect is that, by using the design information of the sample to analyze the circuit pattern structure, the structure can be analyzed without receiving an influence of image quality or the like, and non-defective product images can be stably synthesized from a defect image. As a result, defect observation can be performed with high throughput without taking a non-defective product image.

BRIEF DESCRIPTIONS OF THE DRAWINGS

BEST MODE FOR CARRYING OUT THE INVENTION

Hereinafter, embodiments of the present invention will be described in detail with reference to the accompanying drawings. Note that components having the same function are denoted by the same reference symbols throughout the drawings for describing the embodiments, and the repetitive description thereof will be omitted.

First Embodiment

Figure 1:
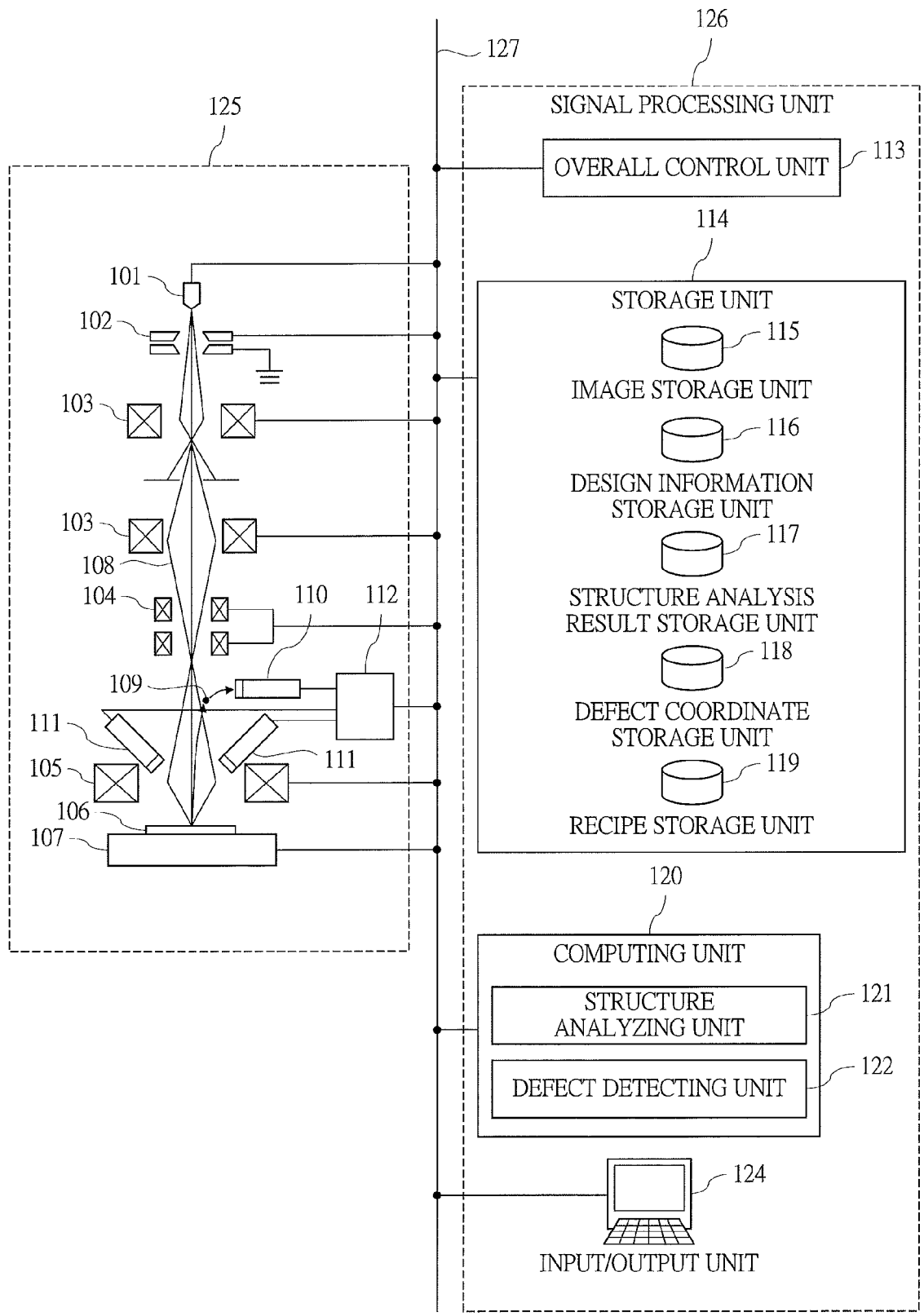
FIG. 1 is a configuration diagram showing a configuration of a defect observation apparatus according to a first embodiment of the present invention.
Figure 2:
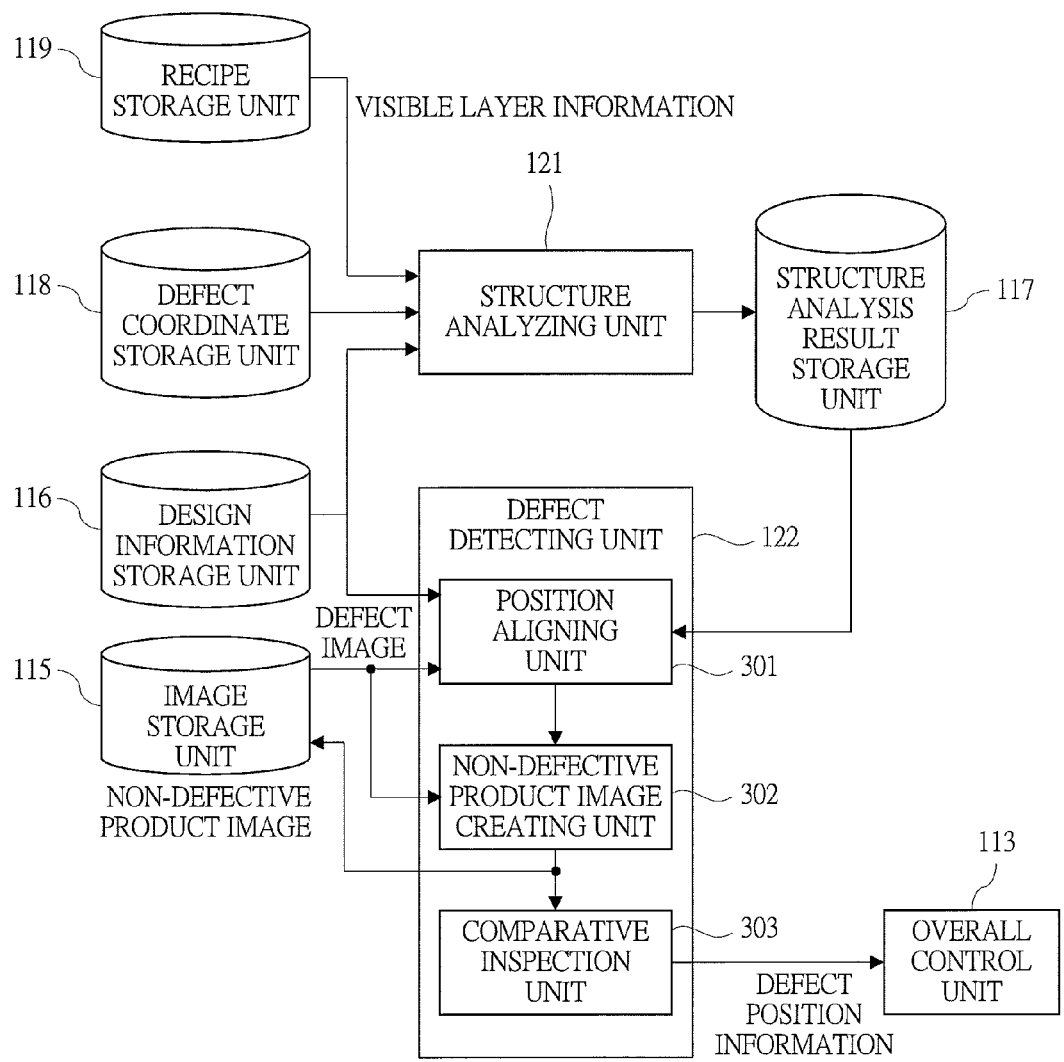
FIG. 2 is a diagram showing details of a computing unit and a data flow in the defect observation apparatus according to the first embodiment of the present invention.

The configuration of a defect observation apparatus according to a first embodiment of the present invention will be described with reference to FIG. 1 and FIG. 2. FIG. 1 is a configuration diagram showing the configuration of the defect observation apparatus according to the first embodiment of the present invention, and FIG. 2 is a diagram showing details of a computing unit and a data flow in the defect observation apparatus according to the first embodiment of the present invention.

In FIG. 1, the defect observation apparatus is made up of a SEM image obtaining unit 125 and a signal processing unit 126, and the SEM image obtaining unit 125 and the signal processing unit 126 are connected via a bus 127.

The SEM image obtaining unit 125 includes an electron source 101 which generates primary electrons 108, an acceleration electrode 102 for accelerating the primary electrons, a focusing lens 103 for converging the primary electrons, a deflector 104 for subjecting the primary electrons to two-dimensional scanning deflection, an objective lens 105 for converging the primary electrons onto a sample 106, a stage 107 movable in an XY plane where the sample is to be mounted, a detector 110 which detects secondary electrons 109 generated from the sample, a detector 111 which detects the primary electrons reflected from the sample surface, and digitizing means 112 for digitizing (A/D converting) a detected signal. Each of these parts is connected through the bus 127 to an overall control unit 113 that controls the overall defect observation apparatus.

The signal processing unit 126 is provided with the overall control unit 113, a computing unit 120, a storage unit 114, devices such as a keyboard and a mouse for providing instructions to the apparatus, and an input/output unit 124 including a monitor, a printer and others which output data from the apparatus, and these units and devices are connected to each other via the bus 127.

The computing unit 120 includes a structure analyzing unit 121 which analyzes a circuit pattern structure from design information of the sample and a defect detecting unit 122 which detects a defect from an image taken so as to include the defect.

Also, the storage unit 114 includes an image storage unit 115 which stores data of taken images, a design information storage unit 116 which stores design information of the sample, a structure analysis result storage unit 117 which stores the results of analyzing a circuit pattern structure from the design information of the sample, a defect coordinate storage unit 118 which stores defect coordinates detected by another inspection apparatus, and a recipe storage unit 119 which stores various electronic optical system conditions in taking images and image processing parameters in defect detection as recipes.

In FIG. 2, the structure analyzing unit 121 of the computing unit 120 stores, for each set of defect coordinates to be observed stored in the defect coordinate storage unit 118, the results of analysis of the circuit pattern structure in the structure analysis result storage unit 117 based on visible layer information stored in the recipe storage unit 119 and the design information stored in the design information storage unit 116.

The defect detecting unit 122 includes a position aligning unit 301 which aligns the positions of the taken defect image and design information of a peripheral area, a non-defective product image creating unit 302 which creates a non-defective product image based on the structure analysis results read from the structure analysis result storage unit 117, and a comparative inspection unit 303 which specifies a defect position by a comparative inspection between an estimated non-defective product image and the defect image, and the defect detecting unit 122 outputs the detected defect position information to the overall control unit 113.

Figure 3:
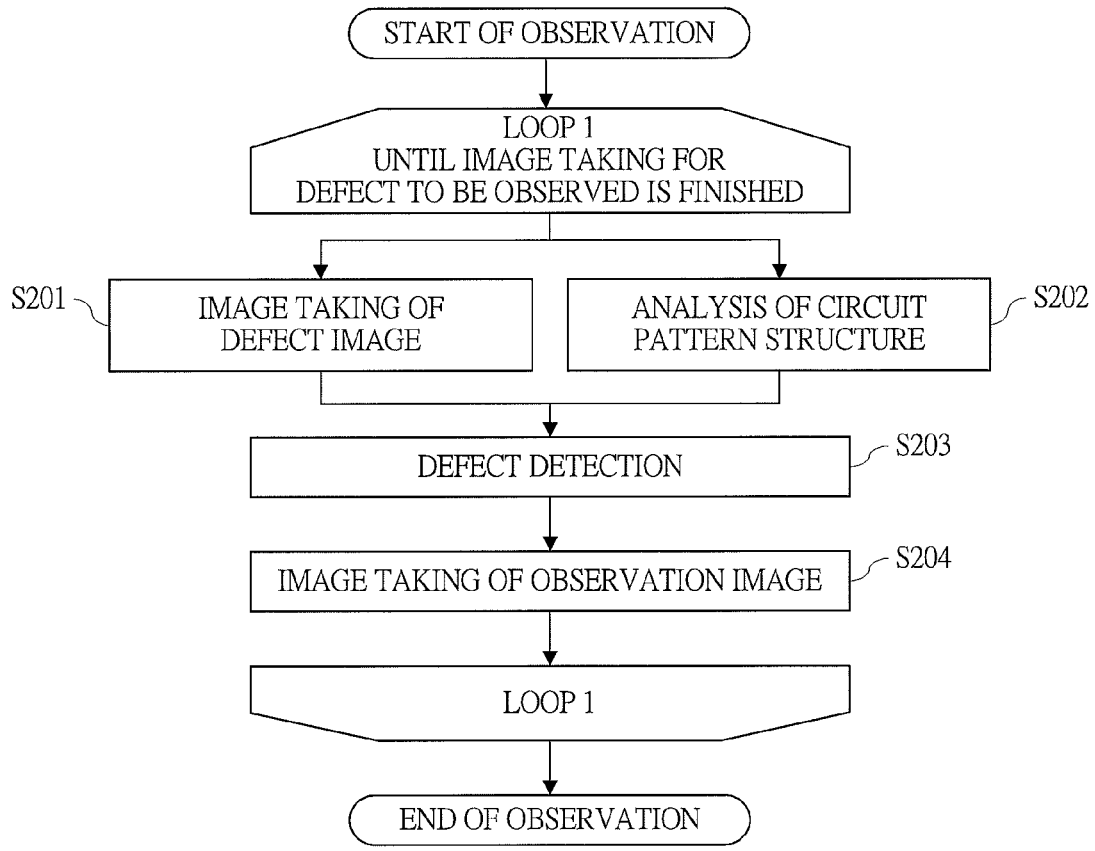
FIG. 3 is a flowchart showing a process at the time of defect observation of the defect observation apparatus according to the first embodiment of the present invention.
Figure 4:
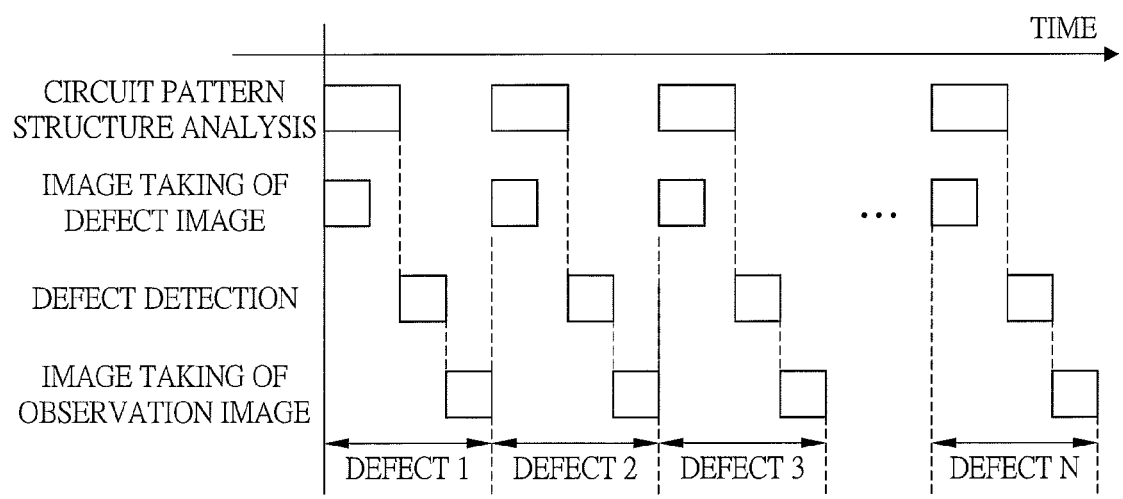
FIG. 4 is a timing chart showing timings at the time of processing of the defect observation apparatus according to the first embodiment of the present invention.
Figure 5:
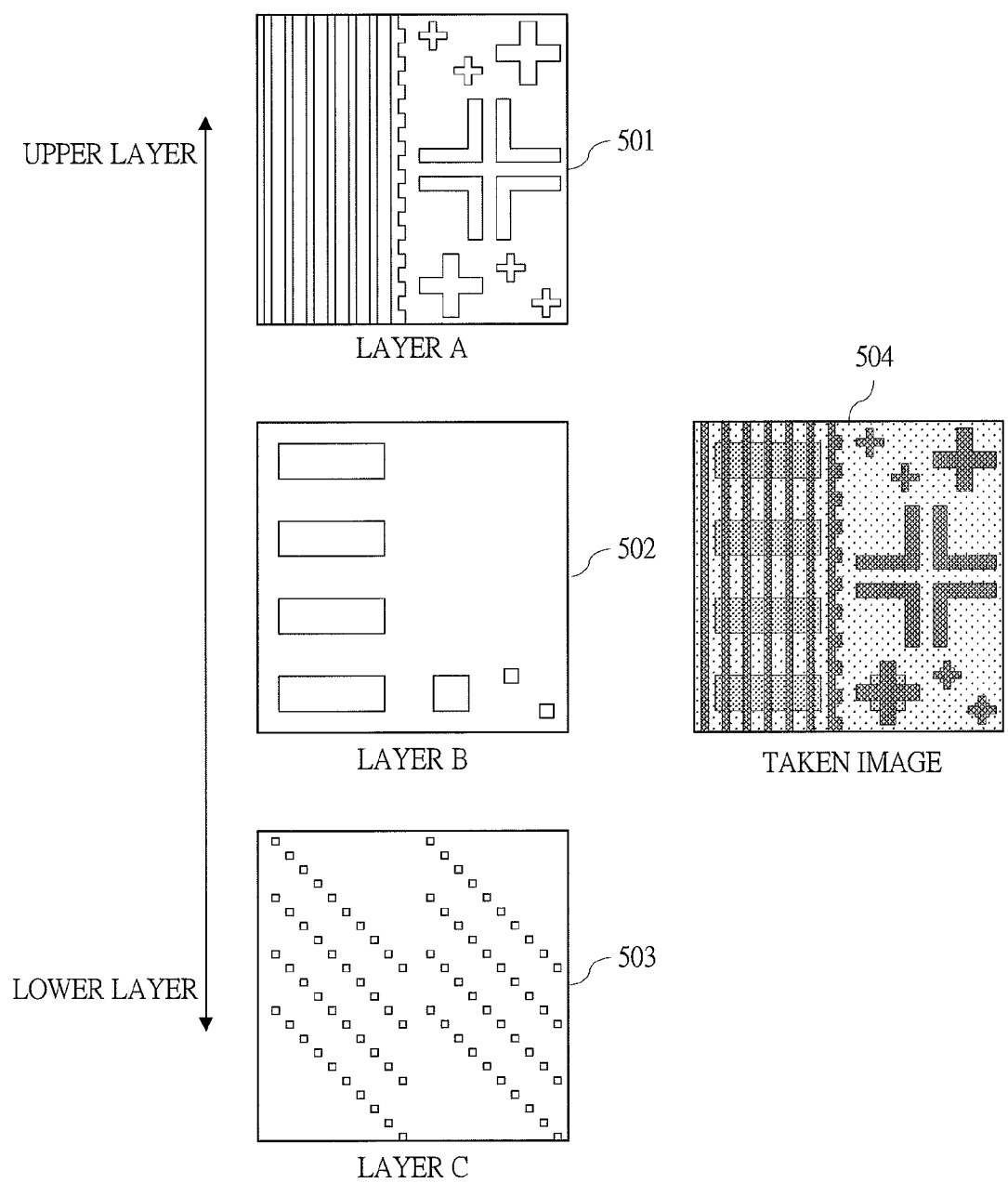
FIG. 5 is a diagram showing an example of layers and taken images included in the design information of the defect observation apparatus according to the first embodiment of the present invention.
Figure 6:
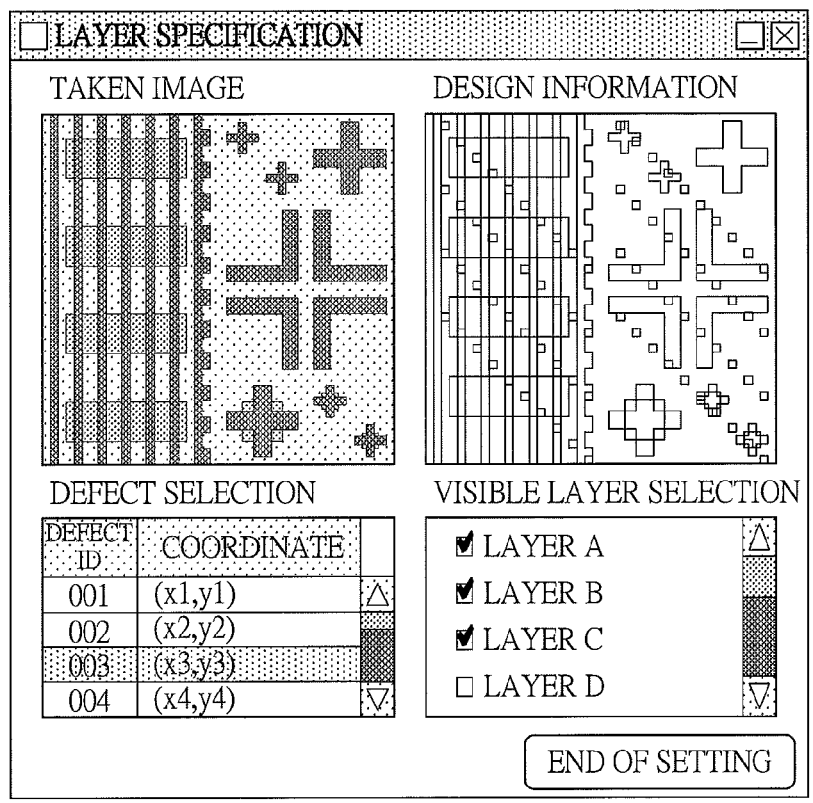
FIG. 6 is a diagram showing an example of an interface for setting visible layer information of the defect observation apparatus according to the first embodiment of the present invention.
Figure 7:
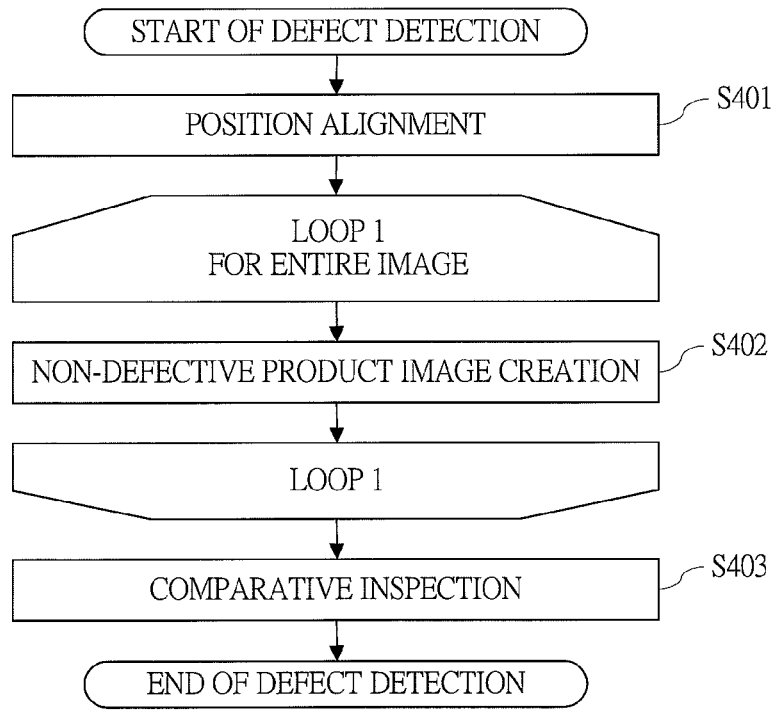
FIG. 7 is a flowchart showing a defect detecting process of the defect observation apparatus according to the first embodiment of the present invention.
Figure 8:
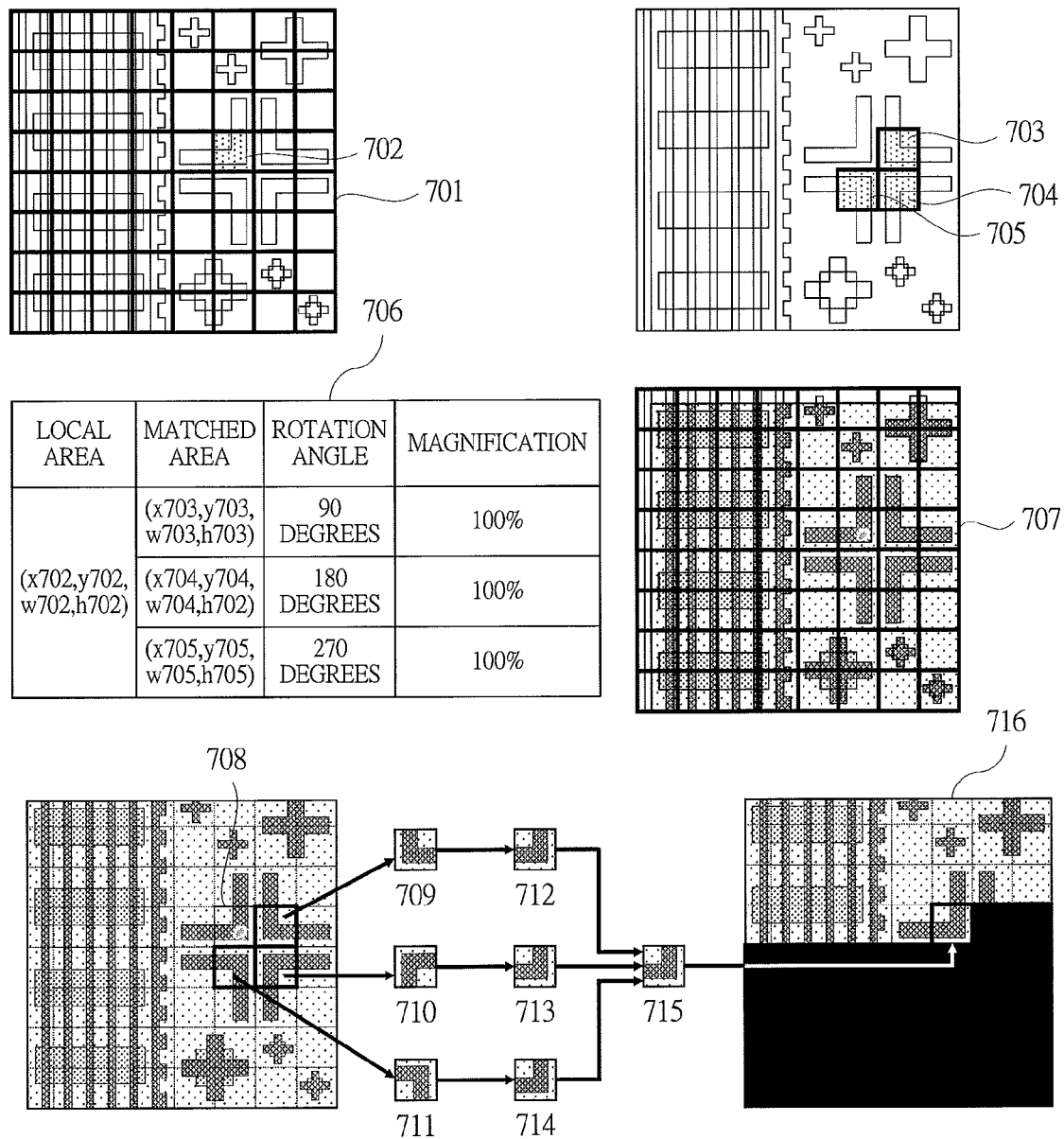
FIG. 8 is a diagram showing a process example of the defect detecting process of the defect observation apparatus according to the first embodiment of the present invention.

Next, a defect observation method of the defect observation apparatus according to the first embodiment of the present invention will be described with reference to FIG. 3 to FIG. 8. FIG. 3 is a flowchart showing a process at the time of defect observation of the defect observation apparatus according to the first embodiment of the present invention, FIG. 4 is a timing chart showing timings at the time of processing of the defect observation apparatus according to the first embodiment of the present invention, FIG. 5 is a diagram showing an example of layers and taken images included in the design information of the defect observation apparatus according to the first embodiment of the present invention, FIG. 6 is a diagram showing an example of an interface for setting visible layer information of the defect observation apparatus according to the first embodiment of the present invention, FIG. 7 is a flowchart showing a defect detecting process of the defect observation apparatus according to the first embodiment of the present invention, and FIG. 8 is a diagram showing a process example of the defect detecting process of the defect observation apparatus according to the first embodiment of the present invention.

In the defect observation method for automatically observing a defect with the defect observation apparatus of the present embodiment, prior to taking images, the sample 106 is first mounted on the stage 107.

An operator selects a recipe for use in taking images from a plurality of recipes registered in the recipe storage unit 119, and instructs the overall control unit 113 to perform ADR under the conditions stored in the recipe through the input/output unit 124.

It is assumed that the recipe stores various electronic optical system conditions in taking images (for example, an acceleration voltage, a probe current, and a magnification for taking images), image processing parameters in defect detection (defect detection sensitivity and visible layer information), and others.

Then, the overall control unit 113 reads coordinate information of defects to be automatically observed from the defect coordinate storage unit 118. By using the read coordinates of each defect, processes at S201 to S204 shown in FIG. 3 are preformed, thereby collecting images for observing details of the defect on the sample (hereinafter, observation images).

Here, the coordinates of the defects to be automatically observed are coordinates of defects detected by another inspection apparatus, and an apparatus shown below or others can be used as such another inspection apparatus.

(i) an apparatus that obtains a signal by using optical means to detect a defect.

(ii) an apparatus that obtains a signal by using means of irradiating the sample with a charged particle beam to detect a defect.

In order to take an image in which details of a defect on the sample can be observed, the image needs to be taken in the following steps.

First, the stage 107 is moved so that defect coordinates are included in an image-taking range of an electronic optical system, and the image is then taken. In general, there is an error of about ±4 [μm] between the defect coordinates detected by the previously performed inspection of another defect inspection apparatus and read from the storage unit 114 and actual defect coordinates.

For this reason, the image is taken at a first magnification with a field of view of about 9 [μm] (for example, 15,000 times) so that a defect is within the field of view. However, when the image is taken at the first magnification, details of the defect cannot be observed. Therefore, defect coordinates are detected from the taken image, and the image of the coordinates of the detected defect is taken at a second magnification (for example, 50,000 times).

As a flow for automatically collecting the observation images, as shown in FIG. 3, for all user-specified defect coordinates to be observed among defect coordinates detected by the inspection of the other inspection apparatus, the processes at S201 to S204 are repeated until images of the defects to be observed have been taken, thereby automatically collecting the observation images.

At S201, an image including a defect (hereafter, a defect image) is taken at the first magnification.

Also, concurrently with taking the image, at S202, the circuit pattern structure in a peripheral area of the defect whose image is to be taken is analyzed by using the structure analyzing unit 121.

Next, at S203, the defect is detected by using the defect detecting unit 122 based on the taken defect image and the analyzed circuit pattern structure. Finally, at S204, an image of the detected defect position is taken at the second magnification to obtain an observation image.

FIG. 4 shows a timing chart when the processes above are performed.

In the timing chart shown in FIG. 4, the circuit pattern structure analysis and the defect image taking are performed simultaneously, and after the circuit pattern structure analysis is finished, a defect is detected, and the observation image taking is then performed.

Here, the visible layer information as an input of the structure analyzing unit 121 will be described.

A semiconductor is manufactured through many processes and has a structure in which circuit patterns formed in the respective processes are stacked. For this reason, a plurality of pieces of circuit pattern information corresponding to the respective processes are described in the design information in general (hereinafter, circuit pattern information for each process is referred to as a layer).

The defect observation is generally performed as appropriate in a manufacturing process, and a layer observable as an image differs depending on the stage of the process of manufacturing a sample to be reviewed. Also, in some cases, the layer observable as an image differs depending on set image-taking conditions. The visible layer information describes a layer observable as an appearance when an image is taken under the set image-taking conditions.

For example, the example of FIG. 5 shows pieces of design information (501 to 503) in a partial area of a semiconductor wafer and an image (504) obtained by taking an image of a corresponding area. As design information, a layer A to a layer C are included. However, only circuit patterns included in upper layers, that is, the layer A (501) and the layer B (502) can be observed from the taken image, and a circuit pattern included in the layer C (503) cannot be observed.

Next, a setting method of visible layer information will be described. In the defect observation apparatus of the present embodiment, the visible layer information can be set as a recipe. As a method for this, an interface as shown in FIG. 6 is provided, in which images taken under the set image-taking conditions and design information corresponding to the image-taken areas are displayed adjacently and layers observable as an appearance can be specified by the user.

By inputting information about the visible layer selection from the input/output unit 124 with the interface as shown in FIG. 6, the visible layer information is set.

Note that it is also possible to automatically set the visible layer information with the design information and others.

Next, the process of analyzing the circuit pattern structure at S202 in FIG. 3 will be described.

The structure analyzing process uses the visible layer information, the defect coordinates, and the design information as inputs and is performed by the structure analyzing unit 121.

First, a peripheral area in the design information is divided into mesh-like local areas. The peripheral area mentioned here is an area which is centered on the defect coordinates detected by the other inspection apparatus and is set based on an image-taken area and an amount of positional shift error at the time of image taking, and is an area larger than the image-taken area.

Then, for each local area, by using design information unified based on the visible layer information, a search is made for the areas designed to have the same appearance in consideration of the rotation and the magnification/reduction. When a search is made for these areas, geometric information of the design information unified based on the visible layer information may be used, or an image made based on the geometric information may be used.

Thus, one or more pieces of the following information obtained as a result of the area search are stored as the result of structure analysis.

(a) an area size and coordinates of the local area.

(b) a size and coordinates of the area found by searching.

(c) a rotation angle required to provide an appearance similar to the local area.

(d) a magnification required to provide the appearance similar to the local area.

Next, the defect detecting process at S203 in FIG. 3 will be described.

The defect detecting process uses the defect image taken so as to include a defect and the results of the circuit pattern structure analysis of the corresponding peripheral area as inputs and is performed by the defect detecting unit 122.

First, as shown in FIG. 7, in a position aligning process at S401, positions of the circuit pattern of the peripheral area and the taken defect image are aligned by using the position aligning unit 301.

In a non-defective product image creating process at S402, a non-defective product image in a local area obtained by dividing the image taken at S201 of FIG. 3 into mesh-like areas is created by using the non-defective product image creating unit 302.

Specifically, an image of one or more areas designed to have the same appearance as a target local area is cut out based on the result of structure analysis, and deformation such as rotation and magnification/reduction is added as appropriate based on the result of structure analysis, thereby creating an average image as a non-defective product image in the target local area.

The process of S402 is repeatedly performed for all local areas, thereby creating non-defective product images of the entire image.

Finally, in a comparative inspection process at S403, a comparative inspection between the defect image and the created non-defective product image is performed by using the comparative inspection unit 303. The comparative inspection may be performed by using the method as described in, for example, Patent Document 1 above.

Next, an example from the circuit pattern structure analysis for one defect to the defect detection will be described with reference to FIG. 8.

The reference numeral 701 in FIG. 8 denotes the result obtained by dividing the design information in the peripheral area into mesh-like local areas. When the areas with similar appearance are searched while focusing on a local area 702 in the circuit pattern structure analysis process at S202 in FIG. 3, an area 703, an area 704, and an area 705 are found as a result of the searching, and a table 706 is obtained as a result of structure analysis for the local area 702 (x702 to x705, y702 to y705, w702 to w705, and h702 to h705 represent x coordinates, y coordinates, area widths, and area heights in the areas 702 to 705, respectively).

In the defect detecting process at S203 of FIG. 3, position alignment between the taken defect image and the design information of the peripheral area is first performed, and a result denoted by 707 of FIG. 8 is obtained.

In an example of the case where the local area 708 is focused in the non-defective product image creating process at S402 of FIG. 7, when images are cut out based on the result of structure analysis 706 from the defect image for the areas where a circuit pattern having the same appearance as the local area 708 is formed, results denoted by 709, 710, and 711 of FIG. 8 are obtained.

Next, deformation is applied to the respective cut-out images based on the result of structure analysis 706, and thus the results denoted by 712, 713, and 714 of FIG. 8 are obtained.

Finally, an average image of these images is created, thereby obtaining a non-defective product image 715 corresponding to the local area 708.

A result denoted by 716 of FIG. 8 is a result of synthesizing non-defective product images partway. By creating the non-defective product images for all the local areas, a non-defective product image corresponding to an entire taken image can be obtained.

As described above, in the present embodiment, since the circuit pattern structure is analyzed by using the design information of the sample, structure analysis can be performed without receiving an influence of image quality, and a non-defective product image can be stably synthesized from a defect image. As a result, defect observation can be performed with high throughput and without taking a non-defective product image.

Second Embodiment

In the second embodiment, every time a non-defective product image is created in each local area obtained by mesh-like division described in the first embodiment, a comparative inspection is performed in an area corresponding to the local area of the defect image, thereby detecting a defect. The configuration of the defect observation apparatus and processes other than the defect detecting process are similar to those of the first embodiment.

Figure 9:
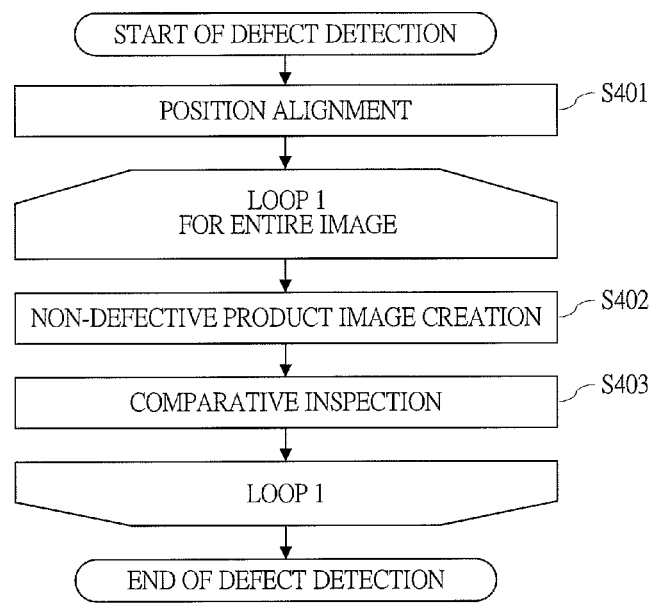
FIG. 9 is a flowchart showing a defect detecting process of a defect observation apparatus according to a second embodiment of the present invention.

A defect detecting process of a defect observation apparatus according to the second embodiment of the present invention will be described with reference to FIG. 9. FIG. 9 is a flowchart showing the defect detecting process of the defect observation apparatus according to the second embodiment of the present invention.

In the first embodiment, in the defect detecting process, after the non-defective product images corresponding to the entire defect image are synthesized, a defect is detected by a comparative inspection. In the second embodiment, however, as shown in FIG. 9, after positions of the circuit pattern in a peripheral area and the taken defect image are aligned by using the position aligning unit 301 in the position aligning process at S401, the non-defective product image creating process at S402 and the comparative inspection process at S403 are performed for each local area obtained by mesh-like division in the entire image.

By this means, in the present embodiment, every time a non-defective product image is created, a defect can be detected by performing a comparative inspection in an area corresponding to the local area of the defect image, and the processing time can be shortened.

Third Embodiment

In the third embodiment, the timings at the time of processing in the first embodiment are changed, and the configuration of the defect observation apparatus and the processes other than the process timing are similar to those of the first embodiment.

Figure 10:
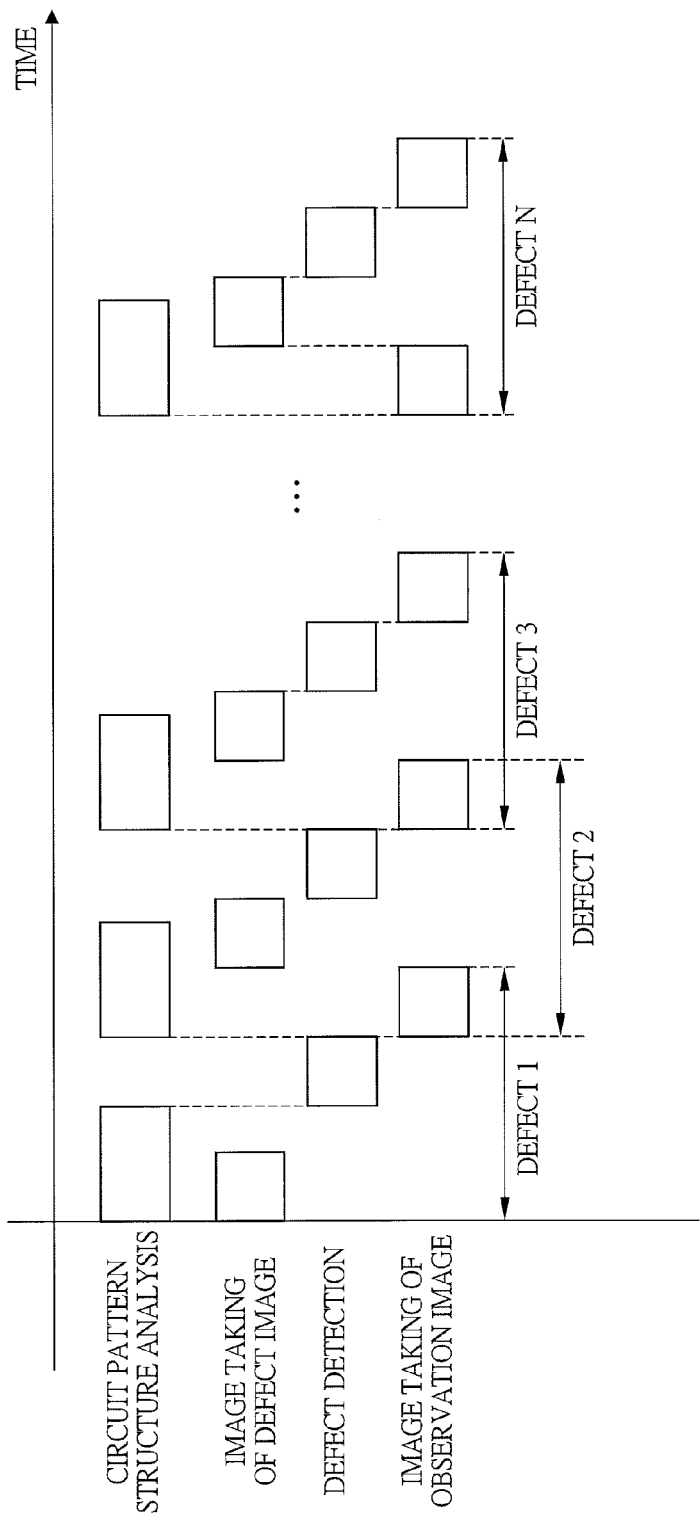
FIG. 10 is a timing chart showing timings at the time of processing of a defect observation apparatus according to a third embodiment of the present invention.

Timings at the time of processing of the defect observation apparatus according to the third embodiment of the present invention will be described with reference to FIG. 10. FIG. 10 is a timing chart showing timings at the time of processing of the defect observation apparatus according to the third embodiment of the present invention.

In the first embodiment, the circuit pattern structure analysis is performed concurrently with taking a defect image. In the present embodiment, however, as shown in FIG. 10, the circuit pattern structure analysis starts at the time of the previous image-taking process of an observation image.

In the present embodiment, since the circuit pattern structure analysis for the next defect is performed when a defect observation image is taken, the processing time can be shortened.

Fourth Embodiment

In the fourth embodiment, the timings at the time of processing in the first embodiment are changed, and the configuration of the defect observation apparatus and the processes other than the process timing are similar to those of the first embodiment.

Figure 11:
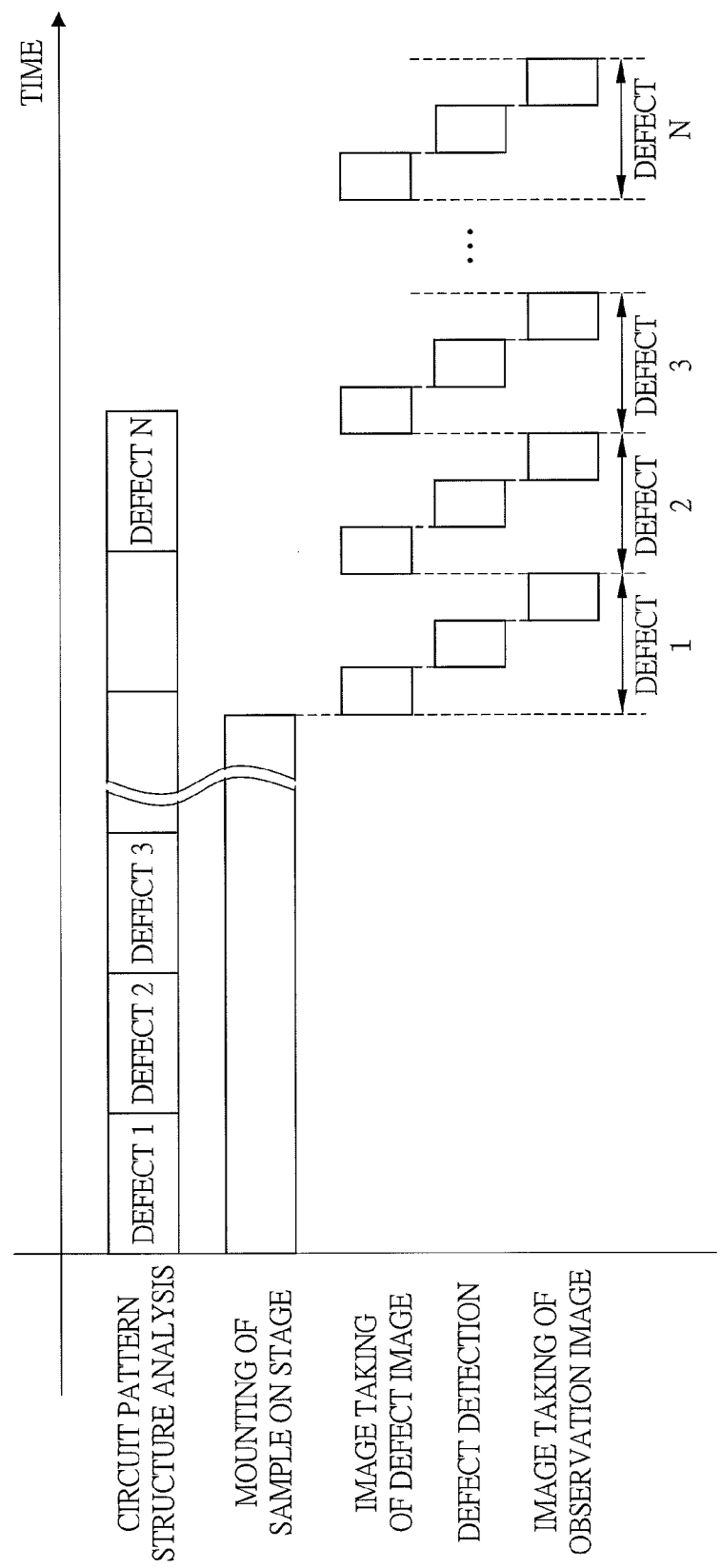
FIG. 11 is a timing chart showing timings at the time of processing of a defect observation apparatus according to a fourth embodiment of the present invention.

Timings at the time of processing of the defect observation apparatus according to the fourth embodiment of the present invention will be described with reference to FIG. 11. FIG. 11 is a timing chart showing timings at the time of processing of the defect observation apparatus according to the fourth embodiment of the present invention.

In the first embodiment, the circuit pattern structure analysis is performed concurrently with taking a defect image. In the present embodiment, however, as shown in FIG. 11, time for mounting the sample to be observed on the stage is also used for the circuit pattern structure analysis.

In the present embodiment, since the circuit pattern structure analysis is performed also during the time for mounting the sample to be observed on the stage, the processing time can be shortened.

INDUSTRIAL APPLICABILITY

In the foregoing, the invention made by the inventors of the present invention has been concretely described based on the embodiments. However, it is needless to say that the present invention is not limited to the foregoing embodiments and various modifications and alterations can be made within the scope of the present invention.

The present invention relates to a defect observation apparatus that observes a defect and others on a sample, and is applicable to apparatuses and systems whose throughputs need to be improved.

DESCRIPTION OF REFERENCE NUMERALS

101: electron source, 102: acceleration electrode, 103: focusing lens, 104: deflector, 105: objective lens, 106: sample, 107: stage, 108: primary electrons, 109: secondary electrons, 110: detector, 111: detector, 112: digitizing means, 113: overall control unit, 115: image storage unit, 116: design information storage unit, 117: structure analysis result storage unit, 118: defect coordinate storage unit, 119: recipe storage unit, 120: computing unit, 121: structure analyzing unit, 122: defect detecting unit, 124: input/output unit, 125: SEM image obtaining unit, 126: signal processing unit, 127: bus, 301: position aligning unit, 302: non-defective product image creating unit, 303: comparative inspection unit

The invention claimed is:

1. A defect observation method in a defect observation apparatus having an image obtaining unit which obtains an image of a sample and a signal processing unit which includes a storage unit and a computing unit, receives an input regarding image information from the image obtaining unit, and observes a defect on the sample with a process by the computing unit, the method comprising the steps of:

receiving an input regarding design information of the sample to be observed from the storage unit;

receiving, based on the design information including one or more layers, an input regarding observable layer information previously set to the sample to be observed from the storage unit;

receiving an input regarding defect coordinates on the sample detected by another inspection apparatus from the storage unit;

analyzing, for a defect on the sample to be observed based on the defect coordinates, a circuit pattern structure in a peripheral area of the defect coordinates based on the design information and the layer information;

taking an image so as to include the defect based on the defect coordinates;

estimating a non-defective product image based on a result of the circuit pattern structure analysis and the image including the defect; and detecting a defect by a comparative inspection between the non-defective product image and the image including the defect, wherein in the circuit pattern structure analysis, the peripheral area centered on the defect coordinates is divided into localized local areas, the respective local areas are searched for those designed to have a similar appearance, and information of a size and coordinates of the local area obtained as a result of the searching is stored as an analysis result in the storage unit.

2. The defect observation method according to claim 1, wherein the defect coordinates on the sample detected by the other inspection apparatus are any of the following defect coordinates:

(i) defect coordinates detected by an apparatus that obtains a signal by using optical means to detect a defect; and (ii) defect coordinates detected by an apparatus that obtains a signal by using means of irradiating the sample with a charged particle beam to detect a defect.

3. The defect observation method according to claim 1, wherein the peripheral area of the defect coordinates is an area which is centered on the defect coordinates detected by the other inspection apparatus and is set based on an image-taken area and an amount of positional shift error at the time of image taking, and is an area larger than the image-taken area.

4. The defect observation method according to claim 1, wherein, in the analysis of the circuit pattern structure, the peripheral area centered on the defect coordinates is divided into localized local areas, the respective local areas are searched for those designed to have a similar appearance, and one or more pieces of following information obtained as a result of the searching are stored in the storage unit as an analysis result:

(a) a size and coordinates of the local area found by searching;

(b) a rotation angle required to provide an appearance similar to the local area; and (c) a magnification required to provide the appearance similar to the local area.

5. The defect observation method according to claim 1, wherein the analysis of the circuit pattern structure is performed concurrently with one or more of following processes:

(1) a mounting process of mounting the sample on a stage of the image obtaining unit;

(2) an image-taking process of taking an observation image after the defect is detected in a previous defect detecting process; and (3) an image-taking process of taking a defect image for detecting the defect.

6. A defect observation apparatus having an image obtaining unit which obtains an image of a sample and a signal processing unit which includes a storage unit and a computing unit, receives an input regarding image information from the image obtaining unit, and observes a defect on the sample, wherein the computing unit receives an input regarding design information of the sample to be observed from the storage unit, receives, based on the design information including one or more layers, an input regarding observable layer information previously set to the sample to be observed from the storage unit, receives an input regarding defect coordinates on the sample detected by another inspection apparatus from the storage unit, analyzes, for a defect on the sample to be observed based on the defect coordinates, a circuit pattern structure in a peripheral area of the defect coordinates based on the design information and the layer information, takes an image so as to include the defect based on the defect coordinates, estimates a non-defective product image based on a result of the circuit pattern structure analysis and the image including the defect, and detects a defect by a comparative inspection between the non-defective product image and the image including the defect, and in the circuit pattern structure analysis, the peripheral area centered on the defect coordinates is divided into localized local areas, the respective local areas are searched for those designed to have a similar appearance, and information of a size and coordinates of the local area obtained as a result of the searching is stored as an analysis result in the storage unit.

7. The defect observation apparatus according to claim 6, wherein the other inspection apparatus is any of following apparatuses:

(i) an apparatus that obtains a signal by using optical means to detect a defect; and (ii) an apparatus that obtains a signal by using means of irradiating the sample with a charged particle beam to detect a defect.

8. The defect observation apparatus according to claim 6, wherein the peripheral area of the defect coordinates is an area which is centered on the defect coordinates detected by the other inspection apparatus and is set based on an image-taken area and an amount of positional shift error at the time of image taking, and is an area larger than the image-taken area.

9. The defect observation apparatus according to claim 6, wherein, in the analysis of the circuit pattern structure, the peripheral area centered on the defect coordinates is divided into localized local areas, the respective local areas are searched for those designed to have a similar appearance, and one or more pieces of following information obtained as a result of the searching are stored in the storage unit as an analysis result:

(a) a size and coordinates of the local area found by searching;

(b) a rotation angle required to provide an appearance similar to the local area; and (d) a magnification required to provide the appearance similar to the local area.

10. The defect observation apparatus according to claim 6 wherein the analysis of the circuit pattern structure is performed concurrently with one or more of following processes:
(1) a mounting process of mounting the sample on a stage of the image obtaining unit;
(2) an image-taking process of taking an observation image after the defect is detected in a previous defect detecting process; and
(3) an image-taking process of taking a defect image for detecting the defect.

\* \* \* \* \*